(12) United States Patent
Pham

(10) Patent No.: US 10,117,826 B2
(45) Date of Patent: Nov. 6, 2018

(54) BODILY LUBRICATING AND MOISTURIZING COMPOSITIONS CONTAINING PLANT MUCILAGE

(71) Applicant: Peter Angia Pham, Tomball, TX (US)

(72) Inventor: Peter Angia Pham, Tomball, TX (US)

(*) Notice: Subject to any disclaimer, the term of this patent is extended or adjusted under 35 U.S.C. 154(b) by 119 days.

(21) Appl. No.: 15/087,267

(22) Filed: Mar. 31, 2016

(65) Prior Publication Data

US 2017/0281525 A1  Oct. 5, 2017

(51) Int. Cl.
| | | |
|---|---|---|
| *A61K 36/00* | (2006.01) | |
| *A61K 8/97* | (2017.01) | |
| *A61K 8/64* | (2006.01) | |
| *A61K 8/49* | (2006.01) | |
| *A61K 8/55* | (2006.01) | |
| *A61K 8/34* | (2006.01) | |
| *A61K 8/44* | (2006.01) | |
| *A61K 8/46* | (2006.01) | |
| *A61K 8/60* | (2006.01) | |
| *A61K 8/19* | (2006.01) | |
| *A61K 8/362* | (2006.01) | |
| *A61Q 19/00* | (2006.01) | |
| *A61K 8/02* | (2006.01) | |

(52) U.S. Cl.
CPC .............. *A61K 8/97* (2013.01); *A61K 8/0208* (2013.01); *A61K 8/19* (2013.01); *A61K 8/34* (2013.01); *A61K 8/345* (2013.01); *A61K 8/362* (2013.01); *A61K 8/442* (2013.01); *A61K 8/463* (2013.01); *A61K 8/4953* (2013.01); *A61K 8/55* (2013.01); *A61K 8/602* (2013.01); *A61K 8/645* (2013.01); *A61Q 19/007* (2013.01); *A61K 2800/70* (2013.01); *A61K 2800/87* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 4,014,335 A | 3/1977 | Arnold | |
| 4,154,822 A | 5/1979 | Polimeni et al. | |
| 5,851,963 A | 12/1998 | O'Bryant | |
| 6,124,248 A | 9/2000 | O'Bryant et al. | |
| 8,628,816 B2 | 1/2014 | Henry et al. | |
| 9,163,374 B2 * | 10/2015 | Alcantar | B01J 20/24 |
| 2009/0110789 A1 * | 4/2009 | Mower | A23L 2/38 |
| | | | 426/330.5 |
| 2014/0303094 A1 | 10/2014 | Bastia et al. | |

FOREIGN PATENT DOCUMENTS

| | | | |
|---|---|---|---|
| CN | 102239914 A | * | 11/2011 |
| CN | 105192083 A | * | 12/2015 |
| JP | 5993010 A | | 5/1984 |
| KR | 2012108694 A | * | 10/2012 |
| WO | 2007128578 A1 | | 11/2007 |
| WO | 2008047394 A1 | | 4/2008 |
| WO | 2015030702 A2 | | 3/2015 |

OTHER PUBLICATIONS

Noorlaila et al, Emulsifying properties of extracted okra (*Abelmoschus esculentus* L.) mucilage of different maturity index and its application in coconut milk emulsion. International Food Research Journal (2015), vol. 22, No. 2, pp. 782-787 (Year: 2015).*

Nasipuri et al, Mucilage from *Abelmoschus esculentus* (okra) fruits. A potential pharmaceutical raw material. Part II. Emulsifying properties. Journal of Pharmaceutical Research and Development (1997), 2(1), 27-34 (Year: 1997).*

Inceboz, Tonay et al., Diagnosis and Treatment of Demodectic Blepharitis, Turkiye Parazitoloji Dergisi, 2009, pp. 32-36, vol. 33(1), Turkish Society for Parasitology.

Gao, YY et al., In vitro and in vivo killing of ocular Demodex by tea tree oil, British Journal of Ophthalmology, 2005, pp. 1468-1473, vol. 89.

Gao YY et al., High Prevalence of Demodex in eyelashes with cylindrical Dandruff, Investigative Ophthalmology & Visual Science, 2005, pp. 3089-3094, vol. 46(9).

Sindhu, G., et al., Anti-inflammatory and antioxidative effects of mucilage of *Trigonella foenum graecum* (Fenugreek) on adjuvant induced arthritic rats, Intl. Immunopharm, 2012, pp. 205-211, vol. 12.

Farooq, U. et al., Extraction and Characterization of Okra Mucilage as Pharmaceutical Excipient, Acad. J. Plant. Sci., 2013, pp. 168-172, vol. 6(4).

International Preliminary Report on Patentability dated Mar. 6, 2018, in PCT/US17/24924.

International Search Report and Written Opinion dated Aug. 24, 2017, PCT/US17/24924.

* cited by examiner

*Primary Examiner* — Qiuwen Mi

(74) *Attorney, Agent, or Firm* — Ramey & Schwaller, LLP

(57) ABSTRACT

A body lubricating and moisturizing formulation utilizes a mucilage-containing extract derived from a plant such as okra, *Abelmoschus esculentus* (*Hibiscus esculentus*). The formulation may be provided as a free liquid such as a solution, suspension, foam or spray or alternatively impregnated into an absorbent solid article such as a wipe, swab, a bandage or a gauze. Application of the formulation to a mucosal or external bodily tissue result in the application of a layer of mucilage that lubricates and moisturizes the tissue as well as protects it from external damage from foreign particles and UV irradiation. The formulation may be impregnated into a cloth pad to provide an eyelid wipe.

15 Claims, 1 Drawing Sheet

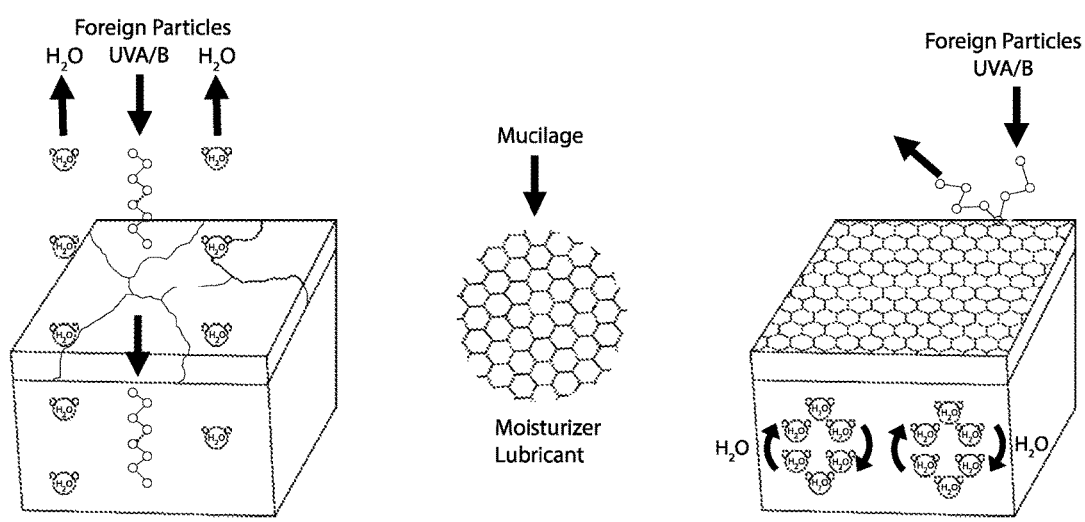

BODILY LUBRICATING AND MOISTURIZING COMPOSITIONS CONTAINING PLANT MUCILAGE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Field of the Invention

The present invention relates generally to the fields of bodily lubrication. More specifically, the present invention provides a formulation comprising plant mucilage for lubricating and moisturizing bodily surfaces, both external and mucosal.

Description of the Related Art

Lubrication plays vital roles in the healthy maintenance of numerous bodily functions. The specific roles vary by the bodily tissue in question.

Tears act as a lubricant for the eyes. Normal ocular function is depending on a clear and smooth layer of tears to support critical ocular surface functions. Tears coat the corneal and conjunctival epithelium to prevent the cells from drying out like those of the skin epithelium, which is a composed of dead cells. With each blink, the tears reduce surface abrasive effect between the eyelid and the corneal surface. The lack of lubrication on the eyes can lead to symptoms of irritation, scratchiness, dryness, and redness. It can also produce scarring, pain, and permanent vision loss.

Saliva is a viscous fluid that acts as the natural lubricant for the mouth. It coats the teeth to prevent tooth decay. It keeps the mouth moist and hydrates food for chewing. The lack of saliva leads to chronic teeth decay, bad breath, swallowing difficulty, and infections.

Even though skin is composed of a layer of dead epithelial cells, lubrication is still needed to maintain the integrity and pliability of the skin. The loss of skin moisture leads to dry, cracked, and flaky skin that increases the risk for infection, bleeding, and pain.

The outer walls of the vagina are coated with a layer of moisture for surface protection, which functions as a natural lubricant for sexual activity and as a barrier to infection and inflammation. The lack of vaginal lubrication can lead to urinary infections, painful intercourse, bleeding, and pain. Lubrication of the rectum performs similar roles.

Mucilage is a viscous gel-like liquid produced by most plants and certain microorganisms. Mucilage is made up of a combination of polysaccharides and proteins. Plants utilize mucilage in diverse life processes such as water storage and seed germination. Individual species of plants vary in the amount of mucilage produced thereby. Examples of plants containing especially high levels of mucilage include various cancti, kelp, various carnivorous plants, mallows, marshmallows, liquorice root, Psyllium, slippery elm bark, and okra, among others.

Okra is a member of the mallow family commonly known for its edible pods rich in mucilage. The current official taxonomic name for okra is *Abelmoschus esculentus*. The *Abelmoschus* genus comprises fifteen species of the mallow family, which were formerly classified within the *Hibiscus* genus. Under the old classification scheme, okra was known as *Hibiscus esculentus*, and this old name is still in common usage. Older classification names for okra from other classification systems include *Abelmoschus bammia; Abelmoschus longifolius; Abelmoschus officinalis; Abelmoschus praecox; Abelmoschus tuberculatus; Hibiscus hispidissimus; Hibiscus longifolius*; and, *Hibiscus praecox*.

The use of okra mucilage as a lubricant for mechanical purposes is known in the previous art. Related U.S. Pat. No. 5,851,963 (O'Bryant, *Organic Lubricant*, Dec. 22, 1998) and U.S. Pat. No. 6,124,248 (O'Bryant, et al., *Organic Lubricants and Coolants*, Sep. 26, 2000) provide biodegradable industrial and machining lubricants and coolants derived from mucilage and mucilage extracts. In one embodiment therein, the mucilage extract is derived from okra, especially okra pods.

U.S. Pat. No. 9,163,374 (Alcantar, et al., *Use of cactus mucilage as a dispersant and absorbant for oil in oil-water mixtures*, Oct. 15, 2015) teaches the use of cactus and *Hibiscus esculentus* mucilage to remove oil contaminants from water. This method is especially intended for use in cleaning up oil spills.

The prior art also includes previous biomedical applications of okra extracts.

U.S. Pat. No. 4,014,335 (Arnold; Randall K., *Ocular Drug Delivery Device*, Mar. 29, 1977) teaches the use of okra gum as one of a number of possible drug carriers in a three-layered laminate ocular drug delivery device taught and claimed therein.

U.S. Pat. No. 4,154,822 (Polimeni et al., *Polysaccharide for Enhancement of Cardiac Output*, May 15, 1979) utilizes olysaccharide substances, preferably derived by extraction and purification of okra plant materials, to provide selective rheological and hemodynamic effects upon biomedical cardiac administration. This method is specifically intended to enhance cardiac output without substantial increments in circulatory (plasma) volume or concurrent inotropic, chronotropic or vasoactive effects.

U.S. Pat. No. 8,628,816 (Henry et al., *Product to reduce glycemic response of carbohydrate based foods*, Jan. 14, 2014) teaches a method for reducing the glycemic index of a premixed flour by adding various pulverized plant materials, including okra, to the flour. The specification of the patent indicates that the mucilage in the okra plays an important role in reducing the glycemic index of the resulting flour.

US Patent Application No. 20140303094 (Bastia et al., *Composition and Use Thereof in the Treatment of Anal Rhagades*, Oct. 9, 2014) teaches a medicament for the treatment of anal rhagades that comprises at least one protein extract and/or at least one beta glucan from hibiscus. The hibiscus in question may be *Hibiscus esculentus*.

The prior art is deficient in the lack of an okra mucilage containing lubricating and moisturizing formulation for external and mucosal body surfaces. The present invention addresses this lack.

SUMMARY OF THE INVENTION

A body lubricating and moisturizing formulation containing plant mucilage is provided by the invention described and claimed herein. More specific embodiments of the described formulation utilize plant mucilage extracted from a species of either the *Abelmoschus* or *Hibiscus* genus, especially mucilage from okra (*Abelmoschus esculentus*, still commonly described by its older scientific classification name *Hibiscus esculentus*)

A number of other components may be included in the formulation to improve its properties and function. *Rubus idaeus* (raspberry) seed oil and *Citrus unshiu* peel extract may be added to provide antioxidant properties. Surfactant activity may be incorporated into the formulation by introducing cocamidopropyl betaine, disodium laureth sulfosuccinate, decyl glucoside, disodium cocoamphodiacetate and/or glycerin. Glycerin may also be added as an emollient in the formulation. *Aloe barbadensis* leaf juice may also be used as an additional emollient. Caffeine is a useful addition for its antioxidation properties. Sodium phytate can be added as a chelating agent. Moisturizers such as hydrolyzed soy protein and ethylhexylglycerin can play useful roles in the formulation. Ethylhexylglycerin also has preservative qualities and can be included along with phenoxyethanol for this purpose.

This formulation may be proved as a free liquid solution, suspension, foam or spray. Alternatively, the formulation can be impregnated onto a wipe, a swab, a bandage, or gauze. An eye wipe comprising a cloth pad wetted with the above formulation is specifically provided and claimed herein.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 illustrates the protective qualities of the lubricating and moisturizing formulation of the instant invention. FIG. 1 shows a biological tissue both before and after the application of the lubricating and moisturizing mucilage formation provided herein. Prior to the application of the mucilage formulation, the tissue is more susceptible to damage by foreign particles and UV rays as well as water loss through evaporation. Application of the mucilage containing lubricating and moisturizing formulation provides a protective barrier against both foreign particles and UV rays as well as aiding in water retention.

DETAILED DESCRIPTION OF THE INVENTION

Therefore, if appearing herein, the following terms shall have the definitions set out below.

Lubricate, as used herein, refers to the addition of anything which reduces friction.

Moisturize, as used herein, describes an action that increases water content or aids in water retention in a biological tissue.

Mucilage, as used herein, is a polysaccharide substance extracted as a viscous or gelatinous solution from plants and microorganisms.

Mucilage may also contain proteins and plays a variety of roles in plant life functions. Isolated mucilage can be used as a lubricant.

As used herein, a surfactant is a chemical compound, usually organic, used to reduce the surface tension between two liquids or between a liquid and a solid. Various detergents, wetting agents, emulsifiers, foaming agents, and dispersants are among the agents that may be used as surfactants.

As described herein. a moisturizer is a chemical substance or combination thereof which hydrates biological tissues, usually by preventing water evaporation from the tissues.

An emollient, as used herein, is a compound or mixture of compounds that are used to moisturize skin to reduce water loss and provide a protective cover. Applications of emollients to skin have a soothing and smoothening effect on the skin, making the skin softer and more pliable.

A conditioning agent, as used herein, refers to any compound or combination thereof, provide a soft improved feel and texture to a biological tissue. Conditioning agents are added to various creams and lotions, gels, serums, facial spray mists, skin toners, shampoos, hair styling gels, hair sprays and hair conditioners.

As used herein, antioxidants are molecules that prevent oxidation. By preventing oxidation, antioxidants protect biological tissues from both the oxidation process itself and from the free radicals that may be produced during the same process. The production of free radicals can result in chain reactions that can result in considerable damage to biological tissues. Various, thiols such as glutathione and ascorbic acid (vitamin C) are examples of antioxidants.

A vasoconstrictor, as used herein, is a chemical agent that narrows blood vessels by contracting the muscular wall of the vessels. This results in reduce blood flow to the affected area. This has a cooling effect on the affected tissue.

A chelating agent is an organic molecule which can bind a metal or metal ion. Chelating agents are useful for removing metal and metal ions from an environment by binding and thus sequestering them.

A buffer, as used herein, refers to anything that stabilizes the pH of a solution. Various chemicals and salt combinations are effective buffers.

A preservative, as used herein, refers to a chemical that is added to products such as food, beverages, pharmaceutical drugs, paints, biological samples, cosmetics, wood, and many other products to prevent either chemical or microbial degradation of the product in question.

The body formulation described and claimed herein is capable of lubricating and moisturizing both mucosal and external biological tissues. The formulation in question utilizes mucilage extracted from plant materials from one or more plant species to achieve this end. The mucilage may be extracted from a number of different types of plant materials including fresh plant material, frozen plant material, dried plant material, and powdered plant material. The concentration of plant mucilage in the formulation may range from 0.001 to 5.0%.

In more specific embodiments of the instant invention, the mucilage containing extract is derived from one or more plant species of either the *Abelmoschus* genus or the *Hibiscus* genus of plant species. In a preferred embodiment of the instant invention, the mucilage is derived from the okra plant, also known by its current scientific name *Abelmoschus esculentus* and formerly known as *Hibiscus esculentus*.

The body lubricating and moisturizing formulation may be buffered to a pH range of 5.5 to 8.0. Buffering the formulation to pH 6.5 is a preferred embodiment of the instant invention. This may be accomplished with a combination of salts including sodium chloride, sodium lactate, potassium chloride, and, calcium chloride. The relative amount of each salt is balanced to achieve the desired pH.

The concentrations of the individual salts may range from 0.001-2.0% in the instant invention.

The formulation of the instant invention may also include surfactants. Possible surfactants and possible concentration thereof include: cocamidopropyl betaine (1.0-12%); disodium laureth sulfosuccinate (1.0-12%);

decyl glucoside (1.0-12.0%); disodium cocoamphodiacetate (0.1-4.0%); and, glycerin (0.008-0.5%). The formulation may also include one or more emollients, which may include aloe barbadensis leaf juice (0.05-4.0%). and glycerin (0.008-0.5%).

One or more antioxidants may be included in the formulation of the instant invention to prevent oxidative damage to the tissues to which it is applied. *Rubus idaeus* (Raspberry) seed oil (0.03-1.0%) and *Citrus unshiu* peel extract (0.01%-1.0%.) are preferred antioxidants.

A number of additional components may be incorporated in the lubricating and moisturizing formulation. Caffeine, at concentration range 0.05-0.5%, may be added as an antioxidant. Sodium phytate (concentration range of 0.02-1.0%) may be included as a chelating agent. Including hydrolyzed soy protein at 0.025-3.0% concentration increases the ability of the formulation to moisturize bodily tissues. 0.001-1.0% ethylhexylglycerin is a useful addition as a preservative carrier agent. The preservative, phenoxyethanol may also be used at a concentration range of 0.01-1.0%.

The body lubricating and moisturizing formulation of the claimed herein may be provided in a number of possible forms. Free liquid forms include solutions, gels, creams, ointments, suspensions, foams, and sprays. Alternatively, the formulation may be impregnated onto a physical object such as a wipe; a swab; a bandage; or, a gauze.

A preferred embodiment of the instant invention is a body lubricating and moisturizing formulation comprising a combination of *Abelmoschus esculentus* (*Hibiscus esculentus*) (okra) mucilage; *Rubus idaeus* (raspberry) seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; caffeine; sodium phytate; hydrolyzed soy protein; phenoxyethanol; ethylhexylglycerin; sodium chloride; sodium lactate; potassium chloride; and, calcium chloride. The above combination may be buffered to a pH range of 5.5 to 8.0, with 6.5 being a preferred pH. The *Abelmoschus esculentus* mucilage may be derived from fresh plant material, frozen plant material, dried plant material, and powdered plant material. The particular embodiment described in the examples provided herein utilizes powdered okra. This solution may be provided as a free suspension or solution, possibly as a foam or spray. Alternatively, the formulation may be provided as liquid absorbed onto a wipe, a swab, a bandage, or gauze.

Another preferred embodiment of the instant invention is an eyelid cleansing and moisturizing eye wipe wetted with the formulation described and claimed herein. Specifically, this formulation is a mixture of *Abelmoschus esculentus* (*Hibiscus esculentus*) (okra) mucilage; *Rubus idaeus* (raspberry) seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; caffeine; sodium phytate; hydrolyzed soy protein; phenoxyethanol; ethylhexylglycerin; sodium chloride; sodium lactate; potassium chloride; and, calcium chloride; wherein said formulation is buffered to a pH range of 5.5 to 8.0. The pH is preferably 6.5.

The following examples are embodiments of the invention and are not meant to limit the present invention in any fashion.

EXAMPLE 1

Body Lubricating Composition

A sample prototype composition of the instant invention was formulated as an aqueous solutions containing a mixture of mucilage extracted from okra (*Abelmoschus esculentus* or *Hibiscus esculentus*) powder; *Rubus idaeus* (raspberry) seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; caffeine; Sodium Phytate; hydrolyzed soy protein; phenoxyethanol; ethylhexylglycerin; sodium chloride; sodium lactate; potassium chloride; and, calcium chloride.

The okra mucilage provides the main lubricating and moisturizing quality of the formulation. The acceptable concentration range for the okra power mucilage is of 0.001-5.0% (w/v). In addition to powered okra, it would be possible to extract the mucilage in the formulated composition from fresh, frozen or dried okra.

The formulation was preferentially buffered to a pH range of 5.5 to 8.0, with a preferable pH of 6.5. The buffering was accomplished with a combination of sodium chloride; sodium lactate; potassium chloride; and, calcium chloride. The concentration ranges of each salt used to attain the desired pH in question were as follows: sodium chloride: 0.3-2.0%; sodium lactate: 0.2-2.0%; potassium chloride: 0.01-2.0%; and, calcium chloride: 0.01-2.0%.

The following agents were incorporated as surfactants in the formulations at the given concentration ranges: cocamidopropyl betaine (1.0-12%); disodium laureth sulfosuccinate (1.0-12%); decyl glucoside (1.0-12.0%); disodium cocoamphodiacetate (0.1-4.0%); and, glycerin (0.008-0.5%). The glycerin provides a dual role in the formation in that it also acts as an emollient. *Aloe barbadensis* leaf juice was also added as another emollient at a concentration range of 0.05-4.0%.

*Rubus idaeus* (Raspberry) seed oil; and, *Citrus unshiu* peel extract were included for their antioxidant properties. The raspberry seed oil was added in concentration range of 0.001-5.0%, while the *Citrus unshiu* peel extract was present at concentrations of 0.01%-1.0%.

Caffeine, at concentration range of 0.05-0.5% was used an antioxidant. Sodium Phytate, a chelating agent, and was added at concentration range of 0.02-1.0%. Hydrolyzed soy protein at a concentrations range of 0.025-3.0% was added as an additional moisturizer.

Ethylhexylglycerin was included as both a moisturizer and a preservative at a concentration range of 0.001-1.0%. The phenoxyethanol was also used as a preservative at concentrations of 0.01-1.0%. Fragrance may be added at concentrations up to 0.25%.

Following the addition of the above components, the remaining aqueous portion of the above described formulation may range 60-95%.

EXAMPLE 2

Wipes

For convenience, cotton pads were impregnated with the above aqueous formulation were prepared. The pads provide a more convenient method of applying the formulation. These pads are especially useful as eye wipes.

EXAMPLE 3

Application of the Formulation to a Biological Tissue.

The lubricating and moisturizing formulation provided herein acts as a lubricating, moisturizing and protective barrier to the tissues to which it is applied. These effects are illustrated in FIGURE 1. The unprotected tissue shown on the left is susceptible to both water loss and assault from foreign particles and UV rays. The application of the lubricating and moisturizing formulations of the instant invention result in a protective layer of mucilage being applied to the surface of the tissue to which it applies. This layer provides a barrier against UV rays and foreign particles. In addition, the resulting barrier prevents water loss from the tissue in question, thereby acting as a moisturizer.

The following references were cited herein:

U.S. Pat. No. 4,014,335, Arnold, Randall K., *Ocular Drug Delivery Device*, Mar. 29, 1977.

U.S. Pat. No. 4,154,822, Polimeni et al., *Polysaccharide for Enhancement of Cardiac Output*, May 15, 1979.

U.S. Pat. No. 5,851,963, O'Bryant, Jeffrey Charles. *Organic Lubricant*, Dec. 22, 1998.

U.S. Pat. No. 6,124,248, O'Bryant, et al., *Organic Lubricants and Coolants*, Sep. 26, 2000.

U.S. Pat. No. 8,628,816, Henry et al., *Product to reduce glycemic response of carbohydrate based foods*, Jan. 14, 2014.

U.S. Pat. No. 9,163,374, Alcantar, et al., *Use of cactus mucilage as a dispersant and absorbant for oil in oil-water mixtures*, Oct. 15, 2015.

US Patent Application No. 20140303094, Bastia et al., *Composition and Use Thereof in the Treatment of Anal Rhagades*, Oct. 9, 2014.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

Changes therein and other uses will occur to those skilled in the art which are encompassed within the spirit of the invention as defined by the scope of the claims.

What is claimed is:

1. A lubricating and moisturizing formulation for application to a bodily tissue, said formulation comprising
    mucilage extracted from *Abelmoschus*, wherein said mucilage is present in the formulation at a concentration of 0.001%-5.0% (w/v);
    one or more emollients; and
    one or more antioxidants;
    caffeine as an antioxidant; sodium phytate as a chelating agent; hydrolyzed soy protein as a moisturizer; and, ethylhexylglycerin as a conditioning agent and preservative; and, phenoxyethanol as a preservative;
    wherein said formulation is intended to be applied to a bodily tissue selected from the group comprising external tissues and mucosal tissues, and said formulation lubricates and moisturizes said bodily tissue.

2. The body lubricating and moisturizing formulation of claim 1, wherein said mucilage is extracted from plant material selected from the group comprising fresh plant material, frozen plant material, dried plant material, and powdered plant material.

3. The body lubricating and moisturizing formulation of claim 1, wherein said formulation is buffered to a pH range of 5.5 to 8.0.

4. The body lubricating and moisturizing formulation of claim 3, wherein said formulation is buffered to a pH of 6.5.

5. The body lubricating formulation of claim 3, where said formulation is buffered with one of more salts selected from the list comprising sodium chloride; sodium lactate; potassium chloride; and, calcium chloride.

6. The body lubricating and moisturizing formulation of claim 1, wherein said formulation further comprises one or more surfactants.

7. The body lubricating and moisturizing formulation of claim 6, where said surfactants are selected from the list comprising cocamidopropyl betaine; disodium laureth sulfosuccinate; decyl glucoside; disodium cocoamphodiacetate; and, glycerin.

8. The body lubricating and moisturizing formulation of claim 1, where said emollients are selected from the list comprising *Aloe barbadensis* leaf juice; and, glycerin.

9. The body lubricating and moisturizing formulation of claim 1, where said antioxidants are selected from the list comprising *Rubus idaeus* seed oil; and, *Citrus unshiu* peel extract.

10. The body lubricating and moisturizing formulation of claim 1, wherein said formulation is provided in a form selected from the group comprising a wipe; a swab; a bandage; a gauze; a suspension; a foam; and, a spray.

11. A body lubricating and moisturizing formulation, said formulation comprising 0.001-5.0% (w/v) *Abelmoschus esculentus* mucilage; *Rubus idaeus* seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; 0.05-0.5% (w/v) caffeine; 0.02-1.0% (w/v) sodium phytate; 0.025-3.0% (w/v) hydrolyzed soy protein; 0.01-1.0% (w/v) phenoxyethanol; 0.001-1.0% (w/v) ethylhexylglycerin; sodium chloride; sodium lactate; potassium chloride; and, calcium chloride; wherein said formulation is buffered to a pH range of 5.5 to 8.0.

12. The body lubricating and moisturizing formulation of claim 11, wherein said *Abelmoschus esculentus* mucilage has been extracted from plant material selected from the group comprising fresh plant material, frozen plant material, dried plant material, and powdered plant material.

13. The body lubricating and moisturizing formulation of claim 12, wherein said *Abelmoschus esculentus* mucilage is extracted from powdered okra.

14. The body lubricating and moisturizing formulation of claim 11, wherein said formulation is provided in a form selected from the group comprising a wipe; a swab; a bandage; a gauze; a suspension; a foam; and, a spray.

15. An eyelid cleansing and moisturizing wipe, said wipe comprising a cloth pad impregnated with a formulation comprising 0.001-5.0% (w/v) *Abelmoschus esculentus* mucilage; *Rubus idaeus* seed oil; *Citrus unshiu* peel extract; *aloe barbadensis* leaf juice; cocamidopropyl betaine; disodium laureth sulfosuccinate; 20 decyl glucoside; disodium cocoamphodiacetate; glycerin; 0.05-0.5% (w/v) caffeine; 0.02-1.0% (w/v) Sodium Phytate; 0253.0% (w/v) hydrolyzed soy protein; 0.01-1.0% (w/v) Phenoxyethanol; 0.001-1.0% (w/v) ethylhexylglycerin; sodium chloride; sodium lactate; potassium chloride; and, calcium chloride; wherein said formulation is buffered to pH 6.5.

* * * * *